(12) United States Patent
King et al.

(10) Patent No.: US 6,603,998 B1
(45) Date of Patent: Aug. 5, 2003

(54) DELIVERY OF MACROMOLECULES INTO CELLS

(75) Inventors: Alan D. King, Takoma Park, MD (US); Richard E. Walters, Columbia, MD (US)

(73) Assignee: Cyto Pulse Sciences, Inc., Hanover, MD (US)

( * ) Notice: Subject to any disclaimer, the term of this patent is extended or adjusted under 35 U.S.C. 154(b) by 0 days.

(21) Appl. No.: 09/889,581

(22) PCT Filed: Jan. 12, 2000

(86) PCT No.: PCT/US00/00014

§ 371 (c)(1),
(2), (4) Date: Jul. 30, 2001

(87) PCT Pub. No.: WO00/44438

PCT Pub. Date: Aug. 3, 2000

Related U.S. Application Data

(60) Provisional application No. 60/117,755, filed on Jan. 28, 1999.

(51) Int. Cl.[7] .................................................. A61N 1/30
(52) U.S. Cl. .......................................... 604/20; 604/501
(58) Field of Search ........................... 604/20, 21, 501, 604/48, 289

(56) References Cited

U.S. PATENT DOCUMENTS

| | | |
|---|---|---|
| 4,832,682 A | 5/1989 | Sarnoff |
| 5,318,514 A | 6/1994 | Hofmann |
| 5,964,726 A | 10/1999 | Korenstein |
| 5,993,434 A | 11/1999 | Dev et al. |
| 6,148,232 A * | 11/2000 | Avrahami .................... 600/372 |
| 6,230,051 B1 * | 5/2001 | Cormier et al. ............. 600/573 |
| 2002/0058936 A1 * | 5/2002 | Avrahami et al. ............. 606/41 |

* cited by examiner

*Primary Examiner*—Brian L. Casler
*Assistant Examiner*—Catherine Serke
(74) *Attorney, Agent, or Firm*—Marvin S. Towsend

(57) ABSTRACT

An object of the invention is to provide a method for delivery of macromolecules into biological cells, such as Langerhans cells (22) in the epidermis (20) of a patient, which includes the steps of coating electodes (16) in an electrode assembly (12) with solid phase macromolecules to be delivered, such as a DNA, and/or RNA vaccine or a protein-based vaccine, attaching the electrode assembly (12) having the coated electrodes (16) to an electrode assembly holder (13), providing a waveform generator (15), establishing electrically conductive pathways between the electrodes (16), and the waveform generator (15), locating the electrodes (16) such that the biological cells are situated therebetween, such as by penetrating the needle electrode (16) into the epidermis (20) above the epidermal basal lamina, and providing pulse waveform from the waveform generator (15) to the electrodes (16), such that macromolecule on the electrodes (16) is driven off of the electrodes (16), and delivered into the biological cells, such as the Langerhans cells (22).

61 Claims, 6 Drawing Sheets

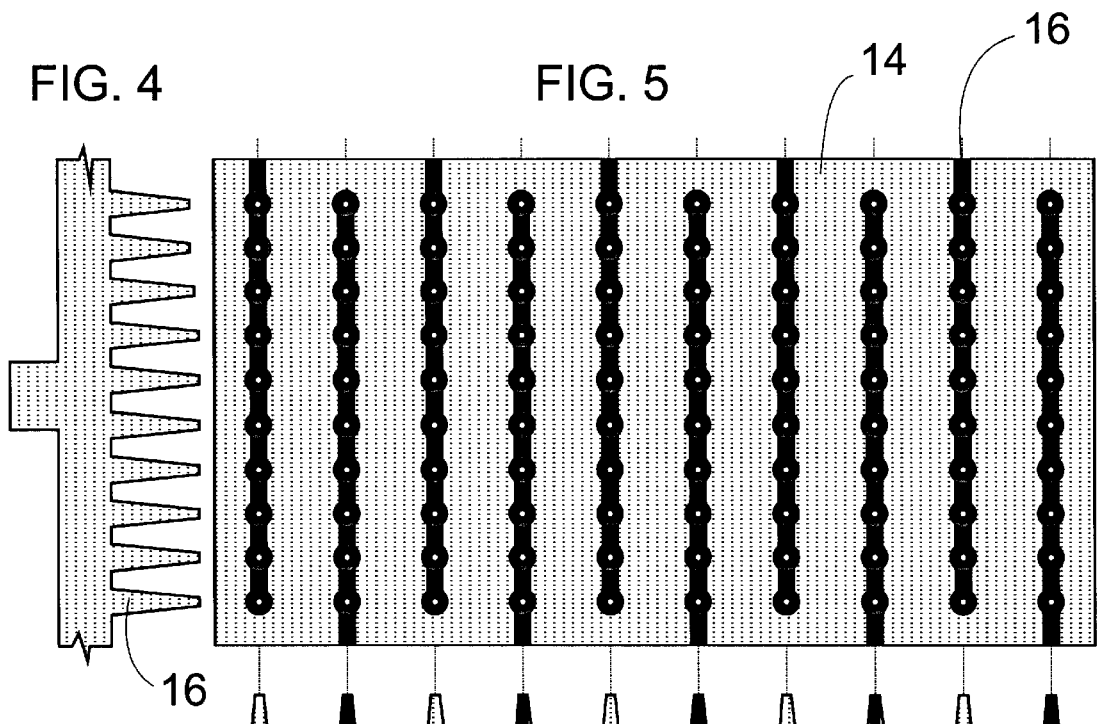

DELIVERY OF MACROMOLECULES INTO CELLS

CROSS-REFERENCE TO RELATED APPLICATION

This application claims priority based upon copending U.S. Provisional Application Ser. No. 60/117,755, filed Jan. 28, 1999.

TECHNICAL FIELD

The present invention relates generally to methods and apparatus for delivery of macromolecules into cells. More specifically, the present invention provides methods and apparatus for delivering substances, such as macromolecules, e. g. polynucleotide vaccines (DNA vaccine and/or RNA vaccine) and protein-based vaccines, into selected cells in epidermal tissue with reduced sensation (reduced pain).

BACKGROUND ART

The first DNA vaccination procedure in the prior art was called naked DNA vaccination because a liquid solution of DNA was injected into the muscle of mice with no additives to enhance transfection. This method does transfect a few cells and does induce an immune response to the expressed antigen in mice. However, in humans and primates, the method does not work well.

In the prior art, an improvement in DNA vaccine efficiency was obtained by the use of a biolistic method for DNA delivery. The biolistic method is done by coating metal microbeads with DNA and shooting the particles into skin after accelerating the particles to a chosen velocity. This method works much better than naked DNA. Part of the reason is that the DNA coated particles are injected into the skin to a depth that increases the chance of transfecting Langerhans cells. However, the biolistic method has some disadvantages. First, it causes some skin damage that may scar in some individuals. Second, in spite of the increased efficiency, more efficiency is needed. Third, the ballistic particle remains inside the patient after treatment. In this respect, it would be desirable if a method for delivering DNA to biological cells were provided which does not cause skin damage that results in scarring. Also, it would be desirable if a method for delivering DNA to biological cells were provided which does not leave a residue of ballistic particles in cells that are treated. As a matter of interest, the following U.S. patents disclose biolistic methods: U.S. Pat. Nos. 5,036,006 and 5,478,744.

A number of additional approaches to delivering macromolecules to biological cells are disclosed in the prior art and are represented by the following U.S. patents or other publications as follows.

U.S. Pat. No. 5,019,034 of Weaver et al discloses a process for electroporation of tissues in which electrodes are placed on top of the tissue surface, such as skin, of a patient. Molecules that are used for treating the skin are placed in reservoirs on top of the skin surface, and the treatment molecules must penetrate into the skin tissues transdermally. That is, the treatment molecules must pass from outside the skin to inside the skin. Not only is the surface layer of the skin relatively impermeable, if the layers of the skin to be treated are near the basal lamina of the epidermis, then the treatment molecules must traverse considerable skin tissue before the cells to be treated are reached by the treatment molecules. Such a treatment method is inefficient for treating cells near the basal lamina. Rather than using electrodes that are placed on the skin surface and have treatment molecules pass through the skin transdermally to treat biological cells near the basal lamina of the epidermis, it would be desirable if an electroporation method were provided for delivering molecules to biological cells in the epidermis, near the basal lamina, without having the treatment molecules pass through the skin transdermally.

U.S. Pat. No. 5,273,525 of Hofmann discloses an apparatus for electroporation of drugs and genetic material into tissues which employs a hollow hypodermic needle for placing the drugs and genetic material in the vicinity of the tissues to be electroporated. Whenever a hollow hypodermic is employed in a tissue, the tissue is cut with a circular cut by the hollow hypodermic needle. As a result, when a patient receives hypodermic injection, the patient has considerable pain. To avoid such a circular cut, and to avoid the considerable pain involved, it would be desirable if a method for delivering molecules to biological cells were provided which does not employ a hypodermic needle.

U.S. Pat. No. 5,318,514 of Hofmann discloses an applicator for the electroporation of drugs and genes into cells. The applicator includes a plurality of needle electrodes which can be penetrated into the skin of a patient. Material to be electroporated into the skin is retained in a fluid reservoir which wets an open cell foam elastomer carrier for the fluid. Because the material to be electroporated is retained in a fluid, in both the reservoir and the open cell foam elastomer, careful control of the amount of the material at the electrode surfaces is difficult. It is difficult to control how much fluid flows down from the reservoir and the open cell foam elastomer to the surfaces of the needle electrodes, and, thereby, it is difficult to control how much of the treatment molecules is actually present on the surfaces of the electrodes 16 as the electroporation process is being carried out on the patient. Moreover, the presence of the fluid medium can have a flushing or washing effect on the tissues that are electroporated in such a way that the electroporation process is interfered with. In these respects, it would be desirable if an electroporation method for delivering molecules to biological cells were provided which does not employ a fluid medium that flows down onto the electrodes as the electroporation process is being carried out on the patient.

Other disclosures relating to the use of electroporation to mediate gene transfer into epidermal cells are found in an article by Reiss et al entitled "DNA-mediated gene transfer into epidermal cells using electroporation" in Biochem. Biophys. Res. Commun., Vol. 137, No. 1, (1986), pages 244–249 and in an article by Titomirov entitled "In vivo electroporation and stable transformation of skin cells of newborn mice by plasmid DNA" in Biochim. Biophys. Acta., Vol. 1088, No. 1, (1991), pages 131–134.

U.S. Pat. No. 5,389,069 of Weaver discloses a method and apparatus for in vivo electroporation of tissues which employs a hollow cylindrical needle for providing treating substances deep into tissues. As mentioned above, avoiding the use hollow cylindrical needles would be desirable to avoid the pain involved therewith.

U.S. Pat. Nos. 5,580,859 and 5,589,466, both of Felgner et al, disclose a method of delivering macromolecules into muscles and skin of a patient by an injection method. Their method does not employ electroporation.

U.S. Pat. No. 5,697,901 of Eriksson discloses gene delivery into tissues by the use of a gene-carrying fluid medium that is pressurized in conjunction with hollow microneedles.

Problems of control and flushing using fluid media have been discussed hereinabove. An electroporation step is not employed in the Eriksson patent. As a matter of interest, Eriksson addresses the subject of pain in two respects. There is a statement that the hollow microneedle system can be used for treating pain. There is a statement that pain in wounds can be relieved by cooling. It is noted by the present inventors herein that Eriksson does not discuss his treatment method per se as being of a pain free or reduced pain treatment method. The present inventors theorize that the pressurized fluid injection method that is employed by Eriksson is not conducive to a pain free or reduced pain treatment method. In this respect, it would be desirable to provide a gene therapy treatment method that employs micro-sized needles, but that does not employ a pressurized fluid injection step for injecting fluid into a patient.

In an article by Henry et al entitled "Microfabricated Microneedles: A Novel Approach to Transdermal Drug Delivery" in Journal of Pharmaceutical Sciences, Vol. 87, No. 8, August 1998, pages 922–925, there is a disclosure that an array of microneedles are employed to penetrate the epidermis to leave micro-sized perforations to facilitate transdermal permeability of fluid-carried treatment agents into the microperforated epidermis. Because the microneedles are inserted only a microscopic distance into the epidermis, use of the microneedles is potentially nonpainful. There is no disclosure that the microneedles are to be used as electrodes. Also, an electroporation step is not disclosed in the Henry et al article.

Further with respect to the issue of reduced pain treatment, it is noted that two important electrical parameters in electroporation are closely related to a perceived pain in vivo. One parameter is absolute voltage experienced by the in vivo tissue. Another parameter is the pulse width experienced by the in vivo tissue. In these respects, it would be desirable to provide an electroporation method for delivering molecules to biological cells which applies relatively low absolute voltage to cells undergoing electroporation and which can be used, if desired, to apply pulses having relatively short pulse width to the cells undergoing electroporation.

Still other features would be desirable in a method and apparatus for delivery of macromolecules into epidermal cells. For example, when electrodes are penetrated into the epidermis, the conductive base electrode portions and the conductive tips of the electrodes may exhibit electrical characteristics which are undesirable with respect to the electroporation process in general and the biological cells that are treated in particular. In this respect, it would be desirable if a method and apparatus for delivery of macromolecules into epidermal cells were provided which render nonconductive the base portions and tip portions of the electrodes.

Once electrode assemblies having a plurality of needle electrodes have been employed on a patient, it may be a difficult task to clean and sterilize them for a subsequent use. In this respect, it would be desirable if a method and apparatus for delivery of macromolecules into cells were provided in which the electrode assemblies are disposable.

When disposable electrode assemblies are employed, it would be desirable if the disposable electrode assemblies are packaged in sterile packaging.

Thus, while the foregoing body of prior art indicates it to be well known to use electroporation to deliver molecules to biological cells, the prior art described above does not teach or suggest a method and apparatus for delivery of macromolecules into cells which has most of the following combination of desirable features: (1) does not cause skin damage that results in scarring; (2) does not leave a residue of ballistic particles in cells that are treated; (3) provides an electroporation method for delivering molecules to biological cells in the epidermis, near the basal lamina, without having the treatment molecules pass through the skin transdermally; (4) does not employ a hypodermic needle; (5) does not employ a fluid medium that flows down onto the electrodes as the electroporation process is being carried out on the patient; (6) does not employ a pressurized fluid injection step for injecting fluid into a patient; (7) applies relatively low absolute voltage to cells undergoing electroporation; (8) if desired, can be used to apply pulses having relatively short pulse width to the cells undergoing electroporation; (9) renders the base portions and tip portions of the electrodes nonconductive; (10) provides disposable electrode assemblies; and (11) provides electrode assemblies which are packaged in sterile packaging. The foregoing desired characteristics are provided by the unique method and apparatus for delivery of macromolecules into cells of the present invention as will be made apparent from the following description thereof. Other advantages of the present invention over the prior art also will be rendered evident.

DISCLOSURE OF INVENTION

In accordance with one aspect of the invention, a method is provided for delivery of molecules into biological cells which includes the steps of:

(a) coating electrodes in an electrode assembly with the molecules to be delivered, (b) attaching the electrode assembly having the coated electrodes to an electrode assembly holder, (c) providing a waveform generator, (d) establishing electrically conductive pathways between the electrodes and the waveform generator, (e) locating the electrodes such that the biological cells are situated therebetween, and (f) providing pulse waveforms from the waveform generator to the electrodes, such that molecules on the electrodes are driven off of the electrodes and delivered into the biological cells.

The pulse waveforms may be provided by applying a sequence of at least three single, operator-controlled, independently programmed, DC electrical pulses, to the biological cells. The sequence of at least three DC electrical pulses has one, two, or three of the following characteristics (a) at least two of the at least three pulses differ from each other in pulse amplitude, (b) at least two of the at least three pulses differ from each other in pulse width, and (c) a first pulse interval for a first set of two of the at least three pulses is different from a second pulse interval for a second set of two of the at least three pulses.

Additionally, the method can include a step of providing the electrode assembly holder with electrically conductive pathways between the electrode assembly and the waveform generator.

In addition, the method can include a step of providing the electrode assembly in a sterile package. In such a case, the electrode assembly is removed from the sterile package prior to use.

Further, the method can include the steps of providing the electrodes with electrically insulated outer surface electrode tip portions and electrically insulated outer surface electrode base portions.

The molecules in the electrode coating can be in a solid phase. The molecules in the electrode coating are, preferably, macromolecules. The macromolecules in the electrode coating can include a polynucleotide vaccine (DNA vaccine and/or RNA vaccine) or a protein-based vaccine.

With a variation of the method of the invention, the molecules can be delivered to Langerhans cells in epidermal tissue of a patient with reduced sensation (reduced pain or nearly painless or pain free) to the patient. To provide reduced sensation delivery of molecules to the patient, the following conditions are maintained (a) the pulse waveforms have an absolute applied voltage in a range of 0.1 to 300 volts; (b) the electrodes of opposite polarity are separated by a separation distance in a range of from 50 to 500 microns; and (c) the electrodes are penetrated into the epidermal tissue a distance up to and slightly beyond the basal lamina layer of the epidermal tissue.

The pulse waveforms which drive the coating molecules off of the electrodes are electrophoresis waveforms. The pulse waveforms which deliver the driven-off molecules into the biological cells are electroporation waveforms. Generally, common pulse waveforms both drive the coating molecules off of the electrodes and deliver the driven-off molecules into the biological cells.

The biological cells can be in vivo, ex vivo, or in vitro. More specifically, the biological cells can be in epidermal tissue and can be Langerhans cells in the epidermal tissue.

In accordance with another aspect of the invention, an apparatus is provided for delivery of molecules into biological cells and includes a waveform generator which provides pulse waveforms. An electrode assembly holder is provided, and an electrode assembly is mechanically supported by the electrode assembly holder. The electrode assembly holder is also electrically connected to the waveform generator through electrically conductive pathways. The electrode assembly includes electrodes which are coated with the molecules to be delivered into the biological cells.

The electrode assembly can be removable and replaceable from the electrode assembly holder. In this respect, the electrode assembly includes electrode-assembly-conductive strips. The electrode assembly holder includes holder conductors which are registrable with the electrode-assembly-conductive strips when the electrode assembly is mechanically connected to the electrode assembly holder. Also, the electrode assembly holder includes electrically conductive pathways between the holder conductors and the waveform generator.

With the apparatus, a sterile package can be provided for the electrode assembly. The sterile package is removed from the electrode assembly after the electrode assembly is mechanically supported by the electrode assembly holder and is electrically connected to the waveform generator.

With the apparatus, if desired, the waveform generator provides pulse waveforms which include a sequence of at least three single, operator-controlled, independently programmed, DC electrical pulses, to the biological cells. The sequence of at least three DC electrical pulses has one, two, or three of the following characteristics (a) at least two of the at least three pulses differ from each other in pulse amplitude, (b) at least two of the at least three pulses differ from each other in pulse width, and (c) a first pulse interval for a first set of two of the at least three pulses is different from a second pulse interval for a second set of two of the at least three pulses.

The electrodes can include electrically insulated outer surface electrode tip portions and electrically insulated outer surface electrode base portions. The electrodes are coated with macromolecules, which may include a polynucleotide vaccine (a DNA vaccine and/or a RNA vaccine) and/or a protein-based vaccine. The polynucleotide vaccine or protein-based vaccine can be a solid form, coating the electrodes, prior to using the electrodes on a patient.

In accordance with yet another aspect of the invention, a packaged sterile electrode assembly is provided which includes a sterile electrode assembly which includes electrodes which are coated with the molecules to be delivered into biological cells. The electrode assembly includes electrode-assembly-conductive strips for connection to complementary electrically conductive pathways leading to the waveform generator. In addition, an internally sterile package encloses the sterile electrode assembly contained therein.

With the packaged sterile electrode assembly, the electrodes can include electrically insulated outer surface electrode tip portions and electrically insulated outer surface electrode base portions.

With the packaged sterile electrode assembly, the electrodes are coated with macromolecules which can include a solid phase polynucleotide (DNA vaccine and/or RNA vaccine) and/or a solid phase protein-based vaccine.

In accordance with the invention, transfection of cells with DNA in vivo, using electric field mediated transfection, is an efficient process. Additionally, electric fields can be used for the delivery of other macromolecules such as RNA and proteins into cells. In the prior art, the electric field delivery has one disadvantage, that being the pain induced by the high voltage electrical pulses required for the transfection. In contrast, as described herein, a method is provided for delivering macromolecules (DNA, RNA, and protein) to cells, in tissues in vivo, using painless (or nearly painless) and efficient electric field mediated delivery.

The electric fields required for electric field mediated DNA transfection, by electroporation, are in the range of 100 volts per cm to 20,000 volts per cm. In accordance with the invention, using a maximum inter-electrode gap of 500 microns (0.5 mm), this range is converted to a range of absolute voltages in a range of 5 to 1,000 volts. Taking into account electrophoresis voltage for driving the DNA off of the electrodes, the range of absolute voltages is in a range of 0.1 to 1,000 volts.

Pain sensation resulting from an electrical stimulus is dependent upon several factors. Among these are voltage, amperage, pulse rise time, pulse width, and pulse frequency. Above a threshold value applied directly to tissues in vivo, increased voltage or increased pulse width will result in an increase in pain.

Two threshold values are important in painless in vivo electric field mediated delivery of macromolecules. A first threshold is the threshold for pain. It is desirable to reduce absolute voltage (and, if desired, also pulse width) applied directly to tissues in vivo below the threshold value for pain. However an opposing second threshold is the minimal electric field required for electric field mediated delivery of macromolecules. Usually, increasing pulse parameters beyond this second threshold value results in increased efficiency in the delivery of macromolecules. An excessive increase will result in cell death.

Fortunately, the important electric field parameter for electric field mediated delivery of macromolecules is volts per cm rather than absolute voltage. To maintain a constant electric field, as the distance between electrodes decreases, the absolute voltage needs to be decreased. Similarly, as the distance between electrode decreases, if the absolute voltage stays the same, the electric field increases. Thus narrowing the distance between electrodes permits a decrease in absolute voltage applied directly to tissues in vivo.

In addition to absolute voltage, pulse width is also important. Very narrow pulse widths significantly increase the threshold voltage required for pain sensation. Electroporation efficiency, within certain limits, is proportional to the product of pulse voltage multiplied by the pulse width. This means that if voltage can be increased, the pulse width can be decreased. Therefore, a decrease in inter-electrode distance also will allow decreased pulse widths to be used.

Another advantage of reduced inter-electrode distance is that fewer dermal nerves are located between the electrodes for the portions of the electrodes that may penetrate through the epidermis into the dermis. For a given applied voltage, the fewer nerves between the electrodes, the less pain is perceived.

Another factor affecting pain is the proximity of the electric field to nerve endings. In the skin, nerves and nerve endings exist throughout the dermis but are absent in the epidermis. However, in the upper papillary layer of the dermis, nerves are relatively few and far between. This means that electrodes that only penetrate the epidermis or epidermis plus upper dermis (papillary layer of dermis) will not be near many nerves. Thus, very short electrodes would induce almost no pain upon insertion nor would pain be induced upon the application of an electric field since the majority of the field is between the electrodes, which are located in the epidermis.

A number of applications of the method and apparatus for delivery of macromolecules into cells, of the invention, are contemplated. Briefly, such applications include polynucleotide vaccination, protein vaccination, and gene therapy.

For DNA vaccination, there are two overriding requirements. One is gene expression in vivo and the other is that at least some of the cells expressing the antigen need to be antigen-presenting cells. The highest concentration of accessible antigen presenting cells resides in the skin as cells called Langerhans cells. These cells are part of a very effective group of antigen presenting cells called dendritic cells. Electroporation is a viable alternative method for transfecting selected cells in vivo.

Proteins also can be introduced into cells using electric field mediated delivery. In conventional vaccination, proteins are delivered outside cells using a hypodermic needle. This type of delivery is inefficient in inducing a cell mediated cytotoxic lymphocyte immune response. Some infectious diseases require a cytotoxic lymphocyte response as a component of the immune response for efficient clearance of the infection. Delivery of proteins into cells promotes the induction of that response.

Delivery of therapeutic genetic medicine into cells for the purpose of making those cells express a missing protein is the basis of gene therapy. The method and apparatus of the present invention can be used to deliver therapeutic DNA into cells on the surface of any accessible organ in addition to the skin. The method of the invention is a method for painless, effective delivery of macromolecules to tissues, in vivo, for the purpose of vaccination (or treatment), DNA vaccination, gene therapy, or other reasons. An electrode with at least one of two characteristics is used for delivery of macromolecules into cells in tissue. One of the two characteristics is an electrode length short enough that it does not penetrate to a depth in tissue with nerve endings. Another characteristic is that inter-electrode distances are small enough to allow pulse parameters (voltage and pulse width) to be used that are painless. Only one or the other of these characteristics is needed in any given application, however, they may be used together.

The above brief description sets forth rather broadly the more important features of the present invention in order that the detailed description thereof that follows may be better understood, and in order that the present contributions to the art may be better appreciated. There are, of course, additional features of the invention that will be described hereinafter and which will be for the subject matter of the claims appended hereto.

In this respect, before explaining a preferred embodiment of the invention in detail, it is understood that the invention is not limited in its application to the details of the construction and to the arrangements of the components set forth in the following description or illustrated in the drawings. The invention is capable of other embodiments and of being practiced and carried out in various ways. Also, it is to be understood, that the phraseology and terminology employed herein are for the purpose of description and should not be regarded as limiting.

As such, those skilled in the art will appreciate that the conception, upon which disclosure is based, may readily be utilized as a basis for designing other structures, methods, and systems for carrying out the several purposes of the present invention. It is important, therefore, that the claims be regarded as including such equivalent constructions insofar as they do not depart from the spirit and scope of the present invention.

In view of the above, it is an object of the present invention to provide a new and improved method and apparatus for delivery of macromolecules into cells which does not cause skin damage that results in scarring.

Another object of the present invention is to provide a new and improved method and apparatus for delivery of macromolecules into cells which does not leave a residue of ballistic particles in cells that are treated.

Even another object of the present invention is to provide a new and improved method and apparatus for delivery of macromolecules into cells that provides an electroporation method for delivering molecules to biological cells in the epidermis, near the basal lamina, without having the treatment molecules pass through the skin transdermally.

Still a further object of the present invention is to provide a new and improved method and apparatus for delivery of macromolecules into cells which does not employ a hypodermic needle.

Yet another object of the present invention is to provide a new and improved method and apparatus for delivery of macromolecules into cells that does not employ a fluid medium that flows down onto the electrodes as the electroporation process is being carried out on the patient.

Still another object of the present invention is to provide a new and improved method and apparatus for delivery of macromolecules into cells which does not employ a pressurized fluid injection step for injecting fluid into a patient.

Yet another object of the present invention is to provide a new and improved method and apparatus for delivery of macromolecules into cells that applies relatively low absolute voltage to cells undergoing electroporation.

Still a further object of the present invention is to provide a new and improved method and apparatus for delivery of macromolecules into cells that can be used, if desired, to apply pulses having relatively short pulse width to the cells undergoing electroporation.

Yet another object of the present invention is to provide a new and improved method and apparatus for delivery of macromolecules into cells which renders the base portions and tip portions of the electrodes nonconductive.

Still a further object of the present invention is to provide a new and improved method and apparatus for delivery of macromolecules into cells that provides disposable electrode assemblies.

Yet another object of the present invention is to provide a new and improved method and apparatus for delivery of macromolecules into cells which electrode assemblies are packaged in sterile packaging.

These together with still other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there are illustrated preferred embodiments of the invention.

BRIEF DESCRIPTION OF DRAWINGS

The invention will be better understood and the above objects as well as objects other than those set forth above will become more apparent after a study of the following detailed description thereof. Such description makes reference to the annexed drawing wherein:

FIG. 4 is a side view of an electrode assembly.

FIG. 5 is a bottom view of the electrode assembly shown in FIG. 4.

FIG. 6 is a partial edge view of the electrode assembly shown in FIG. 5 illustrating the alternate polarity of alternate rows of electrodes.

FIG. 7 is an enlarged top view of the electrode assembly shown in FIG. 4 which shows alternating conductors for contacting alternate rows of electrodes.

MODES FOR CARRYING OUT THE INVENTION

Figure 1:
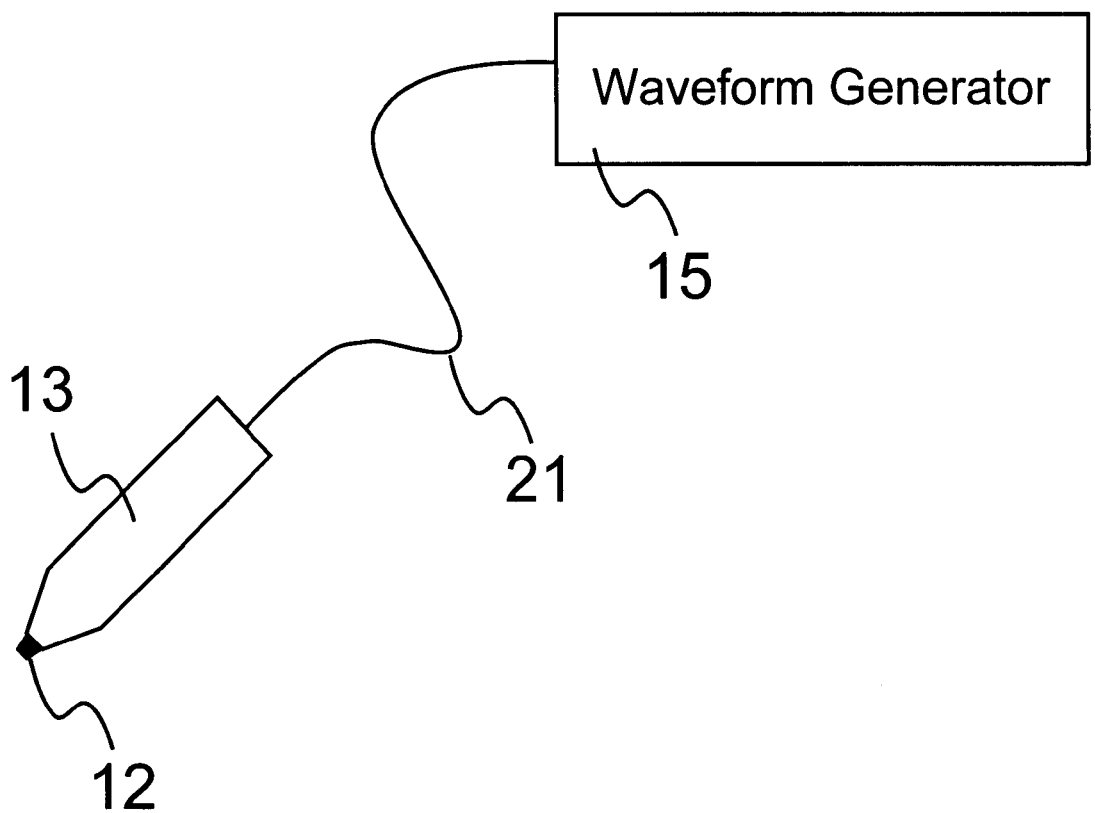
FIG. 1 is a schematic illustration of the overall apparatus of the invention.

A method and apparatus are provided for delivery of macromolecules into cells, and with reference to the drawings, said method and apparatus are described below. The method for delivery of molecules into biological cells employs the apparatus set forth and includes the steps of (a) coating electrodes 16 in an electrode assembly 12 with the molecules to be delivered, (b) attaching the electrode assembly 12 having coated electrodes 16 to an electrode assembly holder 13, (c) providing a waveform generator 15, (d) establishing electrically conductive pathways between the electrodes 16 and the waveform generator 15, (e) locating the electrodes 16 such that the biological cells are situated therebetween, and (f) providing pulse waveforms from the waveform generator 15 to the electrodes 16, such that molecules on the electrodes 16 are driven off of the electrodes 16 and delivered into the biological cells.

In one variation of the method, the molecules are delivered with reduced sensation in a patient to Langerhans cells 22 in the epidermis 20 of a patient. The pulse waveforms have an absolute applied voltage in a range of from 0.1 to 300 volts. Electrodes 16 of opposite polarity are separated by a separation distance in a range of from 50 to 500 microns. The electrodes 16 are penetrated into the epidermal tissue up to and slightly beyond the basal lamina layer of the epidermal tissue.

The pulse waveforms which drive the coating molecules off of the electrodes 16 are electrophoresis waveforms. The electrophoresis waveforms can be in a range of from 0.1 to 100 volts/cm. The pulse waveforms which deliver the driven-off molecules into the biological cells are electroporation waveforms. The electroporation waveforms can be in a range of from 100 to 10,000 volts/cm. Common pulse waveforms both drive the coating molecules off of the electrodes 16 and deliver the driven-off molecules into the biological cells.

The biological cells to which the molecules are delivered can be in vivo, ex vivo, or in vitro. More specifically, the biological cells can be in the epidermis 20 (epidermal tissue) and can be Langerhans cells 22 in the epidermal tissue.

The molecules driven off of the electrodes 16 by electrophoresis electrical pulses are delivered to the cells by electroporation pulses. In accordance with an exemplary protocol, the pulse waveforms are provided by the waveform generator 15 by applying a sequence of at least three single, operator-controlled, independently programmed, DC electrical pulses, to the biological cells. The sequence of at least three DC electrical pulses has one, two, or three of the following characteristics (1) at least two of the at least three pulses differ from each other in pulse amplitude, (2) at least two of the at least three pulses differ from each other in pulse width, and (3) a first pulse interval for a first set of two of the at least three pulses is different from a second pulse interval for a second set of two of the at least three pulses.

The electrode assembly holder 13 is provided with electrically conductive pathways, which includes conductors 21, between the electrode assembly 12 and the waveform generator 15.

The electrode assembly 12 can be provided in a sterile package 24 which is removed from the electrode assembly 12 prior to use.

Preferably, the electrodes 16 have conical tips, whereby they are referred to as needle electrodes. The electrodes 16 can be provided with electrically insulated outer surface electrode tip portions 17 and electrically insulated outer surface electrode base portions 19. The electrically insulated outer surface electrode base portions 19 minimize current flowing across the upper skin surface when the pulse voltage is applied. Moreover, DNA binds poorly to the electrically insulated outer surface electrode base portions 19. The outer surface area of the electrodes 16 between the electrically insulated outer surface electrode tip portions 17 and the electrically insulated outer surface electrode base portions 19 does not have an outer insulation layer and is a good surface for DNA binding. The outer surface areas between the electrically insulated outer surface electrode tip portions 17 and the electrically insulated outer surface electrode base portions 19 is conductive and can be referred to as an active electrode area. The electrically insulated outer surface electrode tip portions 17 prevent large local electric field intensity which may cause burning in the tissue.

An electrode assembly 12 that is suitable for delivering DNA vaccines to Langerhans cells 22 in the epidermis 20 of the forearm has the following characteristics:

(a) electrode length—130 microns (b) electrode material resistivity—less than 0.1 ohm-cm (c) insulation at tip—extending upward 10 microns from tip end (d) insulation at base—extending downward 55 microns from electrode carrier
(e) electrode tip flatness—less than 1 square micron
(f) electrode diameter at base—43 microns
(g) electrode spacing in a conductive row—130 microns
(h) number of electrodes in a conductive row—35
(i) space between conductive rows—260 microns (2×130)
(j) number of conductive rows—25.

For epidermal applications, the lengths of the electrodes 16 are determined by the thickness of the epidermis 20. The thickness of the epidermis 20 varies in different parts of the human body. For example, the thickness of the epidermis 20 on the medial forearm or the lateral upper arm above the deltoid muscle is considerably thinner than the thickness of the epidermis 20 on the heel or sole of the foot.

The molecules in the electrode coating are in a solid phase and are preferably macromolecules 18. The macromolecules 18 in the electrode coating can include a DNA vaccine and/or a protein-based vaccine. The DNA vaccine and the protein-based vaccine can be in the form of a solid phase DNA vaccine or protein-based vaccine applied to the electrodes 16.

Preferably, the electrode assembly 12 is removable and replaceable from the electrode assembly holder 13. The electrode assembly 12 includes electrode-assembly-conductive strips 26. The electrode assembly holder 13 includes holder conductors which are registrable with the electrode-assembly-conductive strips 26 when the electrode assembly 12 is mechanically connected to the electrode assembly holder 13. The electrode assembly holder 13 includes electrically conductive pathways between the holder conductors and the waveform generator 15.

As stated above, there are three main components required for the delivery of macromolecules into cells in tissue. They are a waveform generator 15, an electrode assembly holder 13, and an electrode assembly 12. The waveform generator supplies the electrical pulses necessary for generating the electric field in the tissue. The electrode assembly 12 contains the electrodes 16, and the DNA or protein macromolecules are applied to the electrodes 16. The electrode assembly holder 13 connects the electrode assembly 12 to the waveform generator 15.

The electrode assembly 12 can be in the form of an electrode array can be in the form of a disposable, one-time-use electrode array which has the macromolecules pre-loaded onto the electrodes. In this respect, the pre-loaded electrode array can be provided as a sterile package. To use such an electrode array, the sterile package is opened, and the electrode array is connected to the electrode array holder. The electrode assembly holder is grasped by a person, the electrode assembly is pressed upon the skin of a patient, and the electrode assembly is pressed into the skin of the patient so that the electrode assembly penetrates the stratum corneum of the epidermis. Preferably, the tips of the electrodes in the electrode assembly are located in the region of the Langerhans cells, which are dendritic cells of the epidermis.

Then, a pulse waveform is sent from the waveform generator, through the electrode assembly holder, and to the electrode assembly. The pulse waveform drives pre-loaded macromolecules off of the electrode assembly and into the epidermis. In the epidermis, the pulse waveform electropermeabilizes the target epidermal cells so that the macromolecules enter the target cells.

Figure 2:
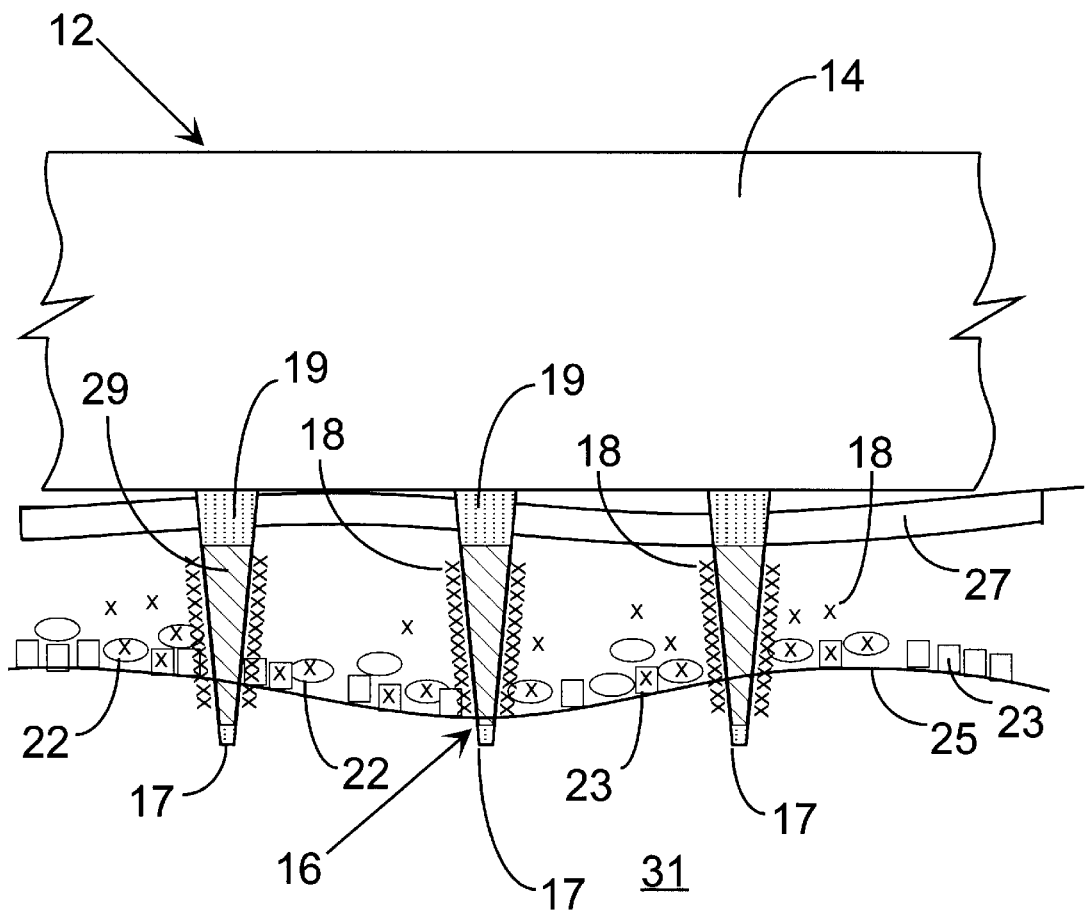
FIG. 2 is a schematic illustration of the pre-coated electrodes of the invention penetrating an epidermal skin layer and being driven by pulse waveforms to deliver macromolecules into epidermal cells.
Figure 3:
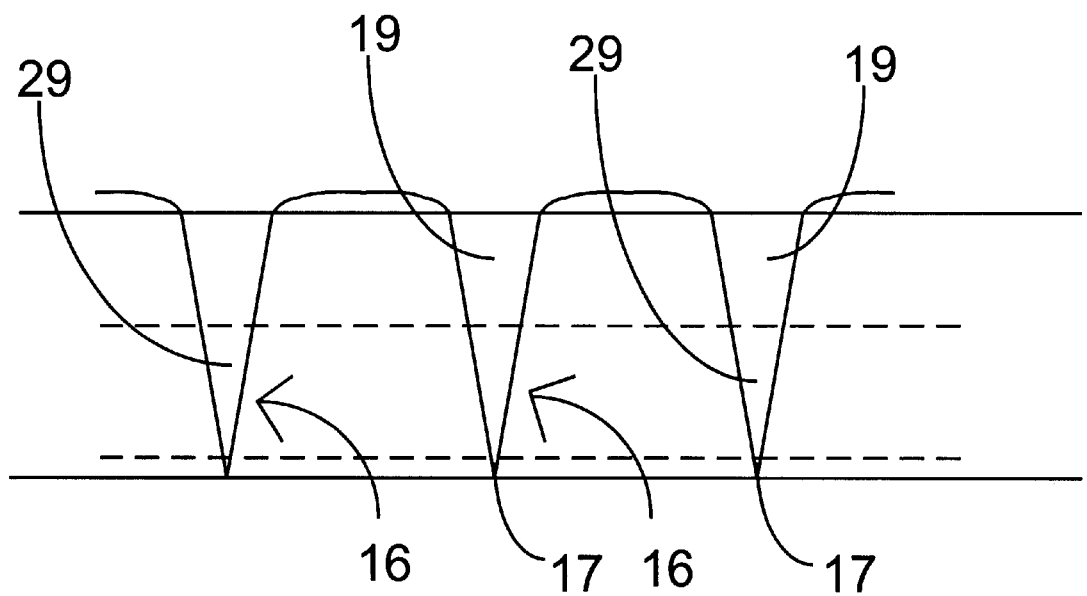
FIG. 3 is a schematic illustration of tip portions of the electrodes.
Figure 8:
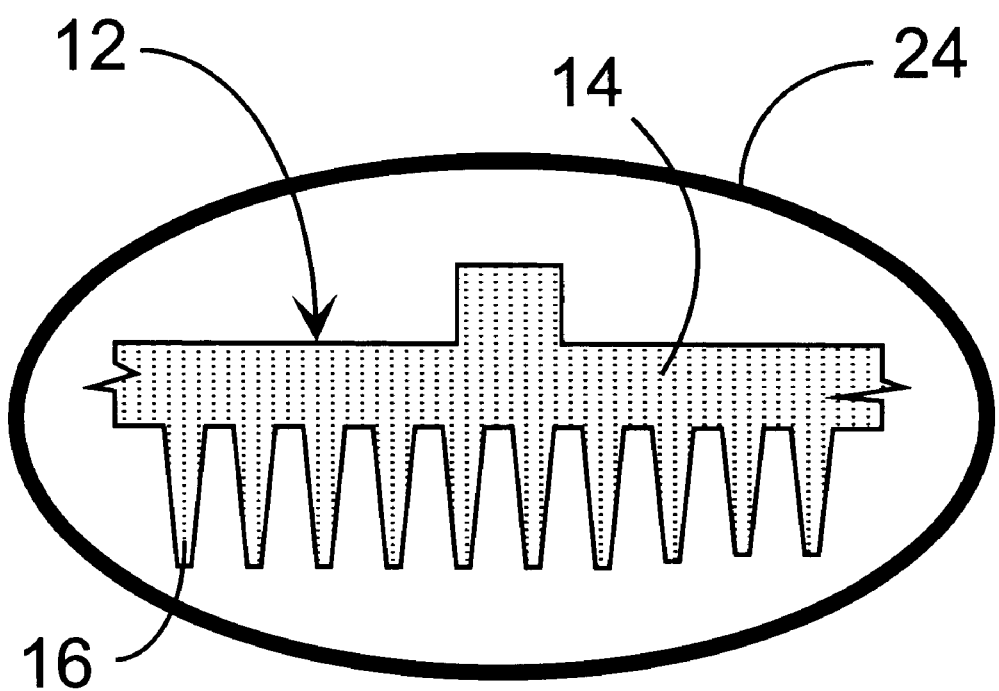
FIG. 8 schematically shows an electrode assembly packaged in a sterile package.

As illustrated in FIG. 2, an electrode assembly 12 includes a non-conductive electrode carrier 14 and a plurality of individual needle electrodes 16 supported by the electrode carrier 14. The active areas 29 of the electrodes 16 are coated with macromolecules which are illustrated as small "x's" 18 on the surfaces of the electrodes 16. Under the influence of the pulse waveforms, some of the macromolecules 18 are driven off of the electrodes 16 by electrophoresis voltage and enter the epidermis 20 and are delivered to the dendritic Langerhans cells 22 and the living epithelial cells 23 in the living epidermis above the basal lamina 25 in the epidermis 20 by electroporation voltage.

The waveform generator 15 produces the pulses for the protocol. The output of the waveform generator can be conventional with a single selection of pulse parameters such as voltage, pulse width, interval between pulses, number of pulses and the vector of the pulse.

Alternatively, the output of the waveform generator can be programmable with the ability to change any of the parameters (voltage, pulse width, interval between pulses, number of pulses,) from pulse to pulse. The variable output is needed for optimal performance because a different electric field is required for macromolecular movement off of the electrodes 16 than the electric field required for electric field mediated delivery of macromolecules into cells. A suitable programmable pulse generator is the PulseAgile (Registered in U.S. Patent and Trademark Office), Model PA-4000 Electroporation System made by Cyto Pulse Sciences, Inc., P.O. Box 609, Columbia, Md. 21045. It is noted that the Model PA-4000 delivers rectangular waves of various amplitudes (voltages), width, and intervals.

In addition to programmable control of voltage, pulse width, interval between pulses and number of pulses from pulse to pulse, programmable control of two other parameters is desired. One is control of the direction or vector of the applied electric field. The other is control of electrode selection. In one application, electric field direction could be reversed to insure better distribution of the macromolecule. In another application, individual pairs of electrode arrays could be sequentially selected.

A suitable device for electrode selection and the selection of electrode field direction is the programmable pulse switch, which is an optional component of the above-mentioned PA-4000 Electroporation System.

The electrode assembly 12 serves two functions. It delivers the macromolecule to the desired site and it delivers the electric field to the tissue. The electrode assembly 12 consists of:
1. a non-conductive electrode carrier 14.
2. an array of needle electrodes 16 fabricated on the electrode carrier 14.
3. Electrode-assembly-conductive strips 26 for electrical connection to the holder conductors on the electrode assembly holder 13 to connect electrically to the waveform generator 15.

In carrying out the method of the invention, the tips of the needle electrodes 16 are pressed against the epidermis 20 of a patient with the needles puncturing the stratum corneum 27 and extending into the epidermis 20 and the upper dermis 31 as shown in FIG. 2.

Referring to FIGS. 4, 5, and 6, the needle array consists of N rows that are conductive. Each needle electrode 16 in a row is connected to all other needles in that row electrically. The rows are be driven by electrical pulses, either:
1. independently
2. in pairs
3. all rows active at one time with one row a cathode, the next row an anode, the next row a cathode, etc.

The electrode assemblies (arrays) needed for electric field mediated macromolecular delivery (for DNA transfection and protein delivery) to Langerhans cells 22 in the epidermis 20 have the following specifications:

1. Multiple conductive rows per array, each needle electrode in a conductive row being electrically connected together.
2. Adjacent rows are electrically isolated from each other.
3. Two to one hundred electrode needle electrodes per conductive row.
4. Needle length is selected to conform to epidermal thickness in area treated.
5. Distance between insulated rows of electrode needles being selected in accordance with voltage applied and electromechanical properties of the tissue penetrated
6. Distance between the nearest electrically linked electrode needles being selected to minimize tissue injury and to maximize electric field.
7. Electrodes can be electrically addressed either individually, in rows, or in groups of rows.

The electrode needles can have many shapes. Examples of needle electrode shapes are: cylindrical needles, flat needles, cone shaped needles, and blade needles. The needles can be pointed rounded or blunt. Each of these shapes can be single or multiple per electrode row The purposes of the electrode assembly holder are to establish an electrical connection between the waveform generator and the electrode assembly and to provide a support for the electrode assembly when the electrode assembly is applied to the patient. It provides a mechanical connection for application to the patient. It also provides a means of delivering the electrode assembly to the patient's tissue while maintaining sterility of the electrode assembly.

The electrode assembly can have the following optional features. It can have a means to provide proper pressure on the electrode assembly to the tissue. It can have indicators that indicate correct application pressure, on-going electrical delivery and completion of electrical delivery. It can have a switch for initiation of the pulse protocol. It can have a means for automatically initiating a pulse protocol when proper pressure is applied to the electrode assembly holder.

As stated above, macromolecules, including DNA and protein macromolecules, need to be driven off of the coated electrodes 16 by electrophoresis voltages so that they can move through the extra-cellular spaces of tissue prior to the application of electroporation pulses for delivering the macromolecules into the targeted biological cells in the tissue.

As stated above, the macromolecules are initially bound to the external surfaces of the electrodes 16. In a mechanical approach to coating the electrodes 16 with macromolecules 18, a relatively high concentration of macromolecules 18 is dissolved or suspended in a solvent or liquid carrier. The electrodes 16 are then dipped into the solution or suspension. Then, the solvent or liquid carrier is evaporated, leaving a solid coating of macromolecules 18 on the electrodes 16. Alternatively, the electrodes 16 are coated by spraying. Other mechanical means of coating the electrodes 16 are possible.

Macromolecules such as DNA bind with good efficiency to many surfaces. The physical and chemical properties of the material can be used to enhance binding to electrode surfaces.

Molecules tend to bind to each other through various molecular interactions, each having a different binding strength. These same forces are active between solid substrates and soluble molecules as well as among molecules in solution. The molecular interactions are:
1. Solvation: Solvent binding. An interaction between the components of a molecule and the solvent molecules.
2. Hydrophobic interaction: A solute-solute interaction as a consequence of the inability to interact with the solvent; an avoidance interaction
3. Van der Walls forces are weak attractions that exist between all molecules. It is effective only at short distances and can be stronger if interactions based upon complementary shape
4. Hydrogen bonds are bonds formed between hydrogen and other molecules such as nitrogen and oxygen.
5. Ionic bonds are attractions based upon attraction of oppositely charged portions of molecules.
6. Covalent bonds are the strongest of molecular bonds.

More specifically with respect to DNA, DNA is both sparingly soluble in water and charged. The organic rings within the nucleotides impart the hydrophobic properties to DNA. The phosphate molecules in the DNA polymer, impart a net negative charge.

The strongest bond between an electrode surface and DNA is the hydrophobic bond. When an electrode has a positive charge, DNA moves towards the electrode thereby enhancing the interaction of DNA with the conductive hydrophobic surface. For delivery, the electrical charge will be reversed. Migration from the electrode surface occurs as soon as the repelling force of like charges exceeds the force of the hydrophobic and other molecular interaction.

DNA can be coated onto specific sites by binding the DNA to metal (such as an electrode surface) or another conductive material through the use of a positive charge. Subsequently, for driving the DNA off of the electrode surface and for subsequently delivering the DNA to biological cells. a negative charge is applied to the same surface. DNA, being negatively charged, will migrate in an electric field toward the positive electrode. This phenomenon is called electrophoresis. If the positive electrode is a hydrophobic surface as are most metals, the positive charge and the hydrophobic interaction will work together to hold the DNA to the surface.

Most macromolecules have a net charge in solution at a pH other than its iso-electric point. DNA, for instance, is negatively charged at physiological pH. This means that a DNA molecule will migrate towards a positive electrode. This property is used to bring the macromolecule in contact with the electrode where binding occurs via the other molecular interactions listed. DNA, for instance, can bind because it is hydrophobic.

Figure 9:
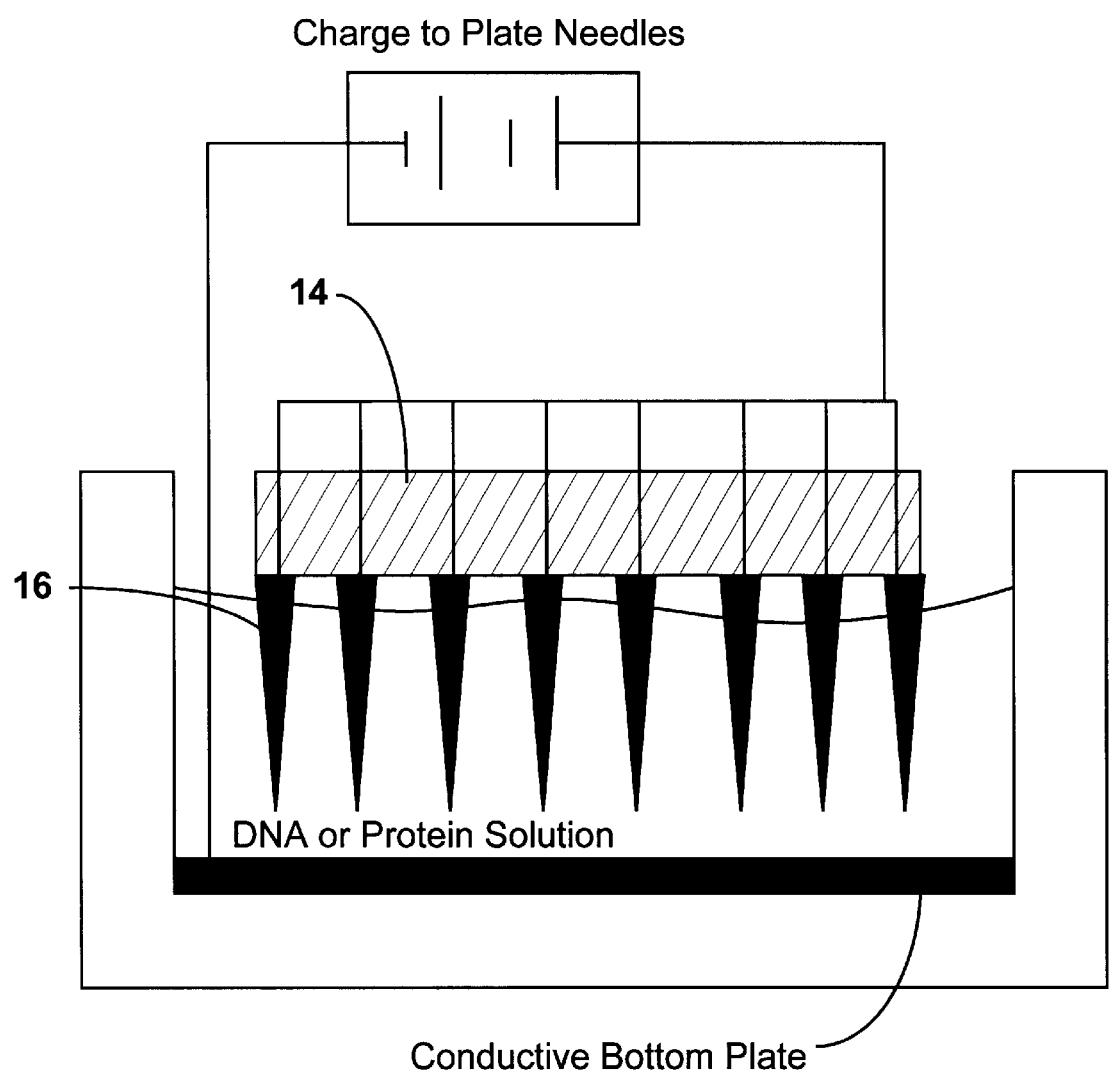
FIG. 9 schematically shows apparatus used for coating the electrodes with macromolecules.

Electrical coating takes advantage of the charge of the macromolecules. A stated above, DNA is negatively charged and therefore migrates to a positively charged electrode. With reference to FIG. 9, which illustrates an apparatus used for coating the electrodes 16, in one coating process, DNA is added to a buffer solution and 30 then placed into a chamber with an electrode that serves as the cathode. Preferably this electrode is separated from the buffer by a gel interface to prevent metal of the cathode coming into contact with the DNA. The electrode device is inserted into the liquid, and a positive charge is applied to the electrode device drawing the DNA to the surface of the electrode device. The DNA attaches to the surface of the electrode device by hydrophobic or other interaction until expelled by a reverse charge. The DNA is dried on to the device with or without a protectant, such as sugars, and with or without other carrier molecules. Substances can also be added to the coating on the electrodes which promote uptake of the treating material into the target cells.

The amount of macromolecule on the electrode assembly varies depending upon the application. For DNA immunization, for example, the electrode assembly is loaded with 0.01 to 100 micrograms of plasmid DNA.

Sterile materials and a sterile local environment can be used in the manufacture of the electrode assembly with the macromolecule. Alternatively, the assembly can be sterilized after manufacture.

A typical sequence of steps in administering macromolecules 18 to a patient using the method and apparatus of the invention are described as follows. In a clinic, the waveform generator 15 would be connected to the electrode assembly holder 13. For an individual application, an electrode assembly 12 whose electrodes 16 have been loaded with the desired macromolecule is selected. The electrode assembly 12 is then mechanically connected to the electrode assembly holder 13. As the electrode assembly holder 13 is grasped by an operator, the electrodes 16 are pressed onto the patient's tissue (typically skin). The electrodes 16 penetrate into the epidermis 20 and extend substantially only to the basal lamina layer. After the electrodes 16 have been located thusly in the epidermis 20, the macromolecular delivery process is started, and the selected pattern of electric fields is initiated. After completion of the delivery protocol, the electrodes 16 are removed from the epidermis 20, and the electrode assembly 12 is discarded.

As stated above, the electrical protocol is designed to drive the macromolecules off of the electrodes 16 into the tissue, followed by delivery of the macromolecules into cells in the tissue. For DNA, a typical sequence of electrical pulses is as follows. First, a series of low voltage (electrophoresis) pulses are applied to the electrodes 16 to remove the DNA from all negatively charged electrodes. Typically, alternating rows of electrodes are negatively charged. Next, higher voltage electroporation pulses are applied to the electrodes 16 to drive the DNA into cells. Next, electrode polarity is reversed and low voltage pulses delivered with opposite polarity to remove the DNA from the remaining electrodes. Higher voltage electroporation pulses are then applied to force the DNA into cells.

A significant use of this macromolecular delivery system is to deliver macromolecules to skin. For this use, electrode needle length is chosen to allow penetration of the electrode to the stratum basalis and basement membrane (basal lamina). Some slight penetration into the dermis may occur. For this use on a patient's arm, an electrode length of 130 microns is selected. This depth allows treatment of cells of the epidermis. For a DNA vaccine or gene therapy, the cells transfected by this delivery method are dendritic cells (skin Langerhans cells 22) and epithelial cells.

Aside from administering macromolecules to biological cells in the epidermis, the method and apparatus of the invention can be used in other biological environments, such as tissues during surgery and with plants.

A wide variety of methods can be employed for manufacturing the electrode assembly 12 of the invention. A number of examples are presented below.

Standard microchip manufacturing processes can be adapted to make the conductive microneedles on a nonconductive support, as in accordance with the invention. In one example, a blank consisting of a silicon or other non conductive layer and a metal layer would be used. The mask would be designed to encourage more etching between rows than within rows, resulting in conductive rows of electrodes with nonconductive spaces between rows.

Another method of construction of an electrode assembly is by adapting the known technique of extrusion microfabrication, and an example follows. Electrode material and adjacent insulating material are prepared by mixing a ceramic, metal or other powder with a thermoplastic binder. The individual components are assembled and warm pressed to stick together. The resulting rod is extruded to reduce its size. Following the extrusion, the new rods are assembled in a rod composed of a multiple of the extruded rod. This newest rod is re-extruded to reduce the size of the multiple rods to the size of the first extruded rod. After the size is reduced to the desired size the parts can be heated to remove the binder. A second, higher heat is used to sinter the metal or ceramic powders together. The rods are cut into disks before or after the sintering. Differential sand blasting or other mechanical or chemical techniques can be used to raise the needles above the surface of the insulator.

Another method for manufacture would be to use laser milling techniques to remove material from a sandwich composed of conductive and nonconductive layers.

For some of the arrays of electrodes, the distance between the electrodes is large enough for mechanical assembly. An example of such assembly follows. Wire of the desired metal composition and diameter is arranged on spools for assembly. The wires are fed into an apparatus that aligns the wire to the correct distance apart. Ceramic or plastic material is injected into a flow through system that results in complete filling of the gap between the electrodes and forms the shape of the outside rim of the electrode. The plastic or ceramic is hardened and cut into discs. The resulting disks are differentially eroded, taking advantage of the softer matrix. The erosion can be done using mechanical methods, chemical methods or a combination of methods. The surface erosion leaves needles of the desired length protruding above the supporting matrix.

Another manufacturing technique is described as follows. Stainless steel needles 30 mm in length and 120 microns in diameter are obtained. One source is from an acupuncture supply company. Seirin No. 02 needles are an example. The needles are cut from the handle if one is present. A number of needles are selected for each row of the device. Thirty-five needles per row are used for this example. The needles are carefully placed side by side with the tips of the needles in line. This step requires care and a jig made of a microscope slide glued at 90 degrees on top of another microscope slide is a tool to help in the alignment. The slide also is be used to check the alignment on a microscope. The needle row (needle bundle) is taped together with 50 micron thick tape. Two or more of the needle bundles are stacked to form an electrode array with the tips of each bundle aligned with the next bundle. The needles are silver soldered to a wire, and alternating needle bundles are connected together electrically. An overall support structure is provided to support the electrode array of needle bundles.

It is apparent from the above that the present invention accomplishes all of the objects set forth by providing a method and an apparatus for delivery of macromolecules into cells that do not cause skin damage that results in scarring. With the invention, a method and an apparatus for delivery of macromolecules into cells are provided which do not leave a residue of ballistic particles in cells that are treated. With the invention, an electroporation method for delivering molecules to biological cells in the epidermis, near the basal lamina, does not have the treatment molecules pass through the skin transdermally. With the invention, a method and an apparatus for delivery of macromolecules into cells are provided which do not employ a hypodermic needle. With the invention, a method and an apparatus for delivery of macromolecules into cells are provided which do not employ a fluid medium that flows down onto the electrodes as the electroporation process is being carried out on the patient.

With the invention, a method and an apparatus for delivery of macromolecules into cells are provided which do not employ a pressurized fluid injection step for injecting fluid into a patient. With the invention, relatively low absolute voltages are applied to cells undergoing electroporation. With the invention, pulses that are applied to the cells can have, if desired, relatively short pulse width to the cells undergoing electroporation. With the invention, a method and an apparatus for delivery of macromolecules into cells are provided which can employ, if desired, electrodes in which the base portions and tip portions of the electrodes are nonconductive. With the invention, a method and an apparatus for delivery of macromolecules into cells provide disposable electrode assemblies. With the invention, a method and an apparatus for delivery of macromolecules into cells are provided in which electrode assemblies are packaged in sterile packaging.

What is claimed is:

1. A method for delivery of molecules into biological cells, comprising the steps of:
   coating electrodes in an electrode assembly with the molecules to be delivered, prior to locating the electrodes such that the biological cells are situated therebetween,
   attaching the electrode assembly having coated electrodes to an electrode assembly holder,
   providing a waveform generator,
   establishing electrically conductive pathways between the electrodes and the waveform generator,
   locating the electrodes such that the biological cells are situated therebetween, and
   providing pulse waveforms from the waveform generator to the electrodes, such that the molecules on the electrodes are driven off of the electrodes and delivered into the biological cells.

2. The method of claim 1 wherein the molecules are delivered into the biological cells using pulse waveforms which have an absolute voltage in a range of from 0.1 to 1,000 volts.

3. The method of claim 1 wherein the molecules are delivered with reduced sensation in a patient to Langerhans cells in epidermal tissue of the patient, wherein the pulse waveforms have an absolute applied voltage in a range of 0.1 to 300 volts, wherein the electrodes, of opposite polarity, are separated by a separation distance in a range of from 50 to 500 microns, and wherein the electrodes are penetrated into the epidermal tissue up to and slightly beyond the basal lamina layer of the epidermal tissue.

4. The method of claim 1 wherein the pulse waveforms which drive the coating molecules off of the electrodes are electrophoresis waveforms.

5. The method of claim 1 wherein the pulse waveforms which drive the coating molecules off of the electrodes are electrophoresis waveforms in a range of from 0.1 to 100 volts/cm.

6. The method of claim 1 wherein the pulse waveforms which deliver the driven-off molecules into the biological cells are electroporation waveforms.

7. The method of claim 1 wherein the pulse waveforms which deliver the driven-off molecules into the biological cells are electroporation waveforms in a range of from 100 to 20,000 volts/cm.

8. The method of claim 1 wherein common pulse waveforms both drive the coating molecules off of the electrodes and deliver the driven-off molecules into the biological cells.

9. The method of claim 1 wherein the biological cells are in vivo.

10. The method of claim 1 wherein the biological cells are ex vivo.

11. The method of claim 1 wherein the biological cells are in vitro.

12. The method of claim 1 wherein the biological cells are in epidermal tissue.

13. The method of claim 1 wherein the biological cells are Langerhans cells in the epidermal tissue.

14. The method of claim 1, further including:
    providing the electrode assembly holder with electrically conductive pathways between the electrode assembly and the waveform generator.

15. The method of claim 1, further including:
    providing the electrode assembly in a sterile package, and
    removing the electrode assembly from the sterile package prior to use.

16. The method of claim 1, further including:
    providing the electrodes with electrically insulated outer surface electrode tip portions.

17. The method of claim 1, further including:
    providing the electrodes with electrically insulate outer surface electrode base portions.

18. The method of claim 1 wherein the molecules in the electrode coating are in a solid phase.

19. The method of claim 1 wherein the molecules in the electrode coating are macromolecules.

20. The method of claim 1 wherein the macromolecules in the electrode coating include a polynucleotide vaccine.

21. The method of claim 1 wherein the macromolecules in the electrode coating include a solid phase polynucleotide vaccine.

22. The method of claim 1 wherein the macromolecules in the electrode coating include a DNA vaccine.

23. The method of claim 1 wherein the macromolecules in the electrode coating include a solid phase DNA vaccine.

24. The method of claim 1 wherein the macromolecules in the electrode coating include a RNA vaccine.

25. The method of claim 1 wherein the macromolecules in the electrode coating include a solid phase RNA vaccine.

26. The method of claim 1 wherein the macromolecules in the electrode coating include a protein-based vaccine.

27. The method of claim 1 wherein the macromolecules in the electrode coating include a solid phase protein-based vaccine.

28. A method for delivery of molecules into biological cells, comprising the steps of:
    coating electrodes in an electrode assembly with the molecules to be delivered,
    attaching the electrode assembly having coated electrodes to an electrode assembly holder,
    providing a waveform generator,
    establishing electrically conductive pathways between the electrodes and the waveform generator,
    locating the electrodes such that the biological cells are situated therebetween, and
    providing pulse waveforms from the waveform generator to the electrodes, such that the molecules on the electrodes are driven off of the electrodes and delivered into the biological cells,
    wherein the pulse waveforms are provided by applying a sequence of at least three single, operator-controlled, independently programmed, DC electrical pulses, to the biological cells, wherein the sequence of at least three DC electrical pulses has one, two, or three of the following characteristics: (a) at least two of the at least three pulses differ from each other in pulse amplitude; (b) at least two of the at least three pulses differ from each other in pulse width; and (c) a first pulse interval for a first set of two of the at least three pulses is different from a second pulse interval for a second set of two of the at least three pulses.

29. A method for delivery of molecules into biological cells, comprising the steps of:
coating electrodes in an electrode assembly with the molecules to be delivered,
attaching the electrode assembly having coated electrodes to an electrode assembly holder,
providing a waveform generator,
establishing electrically conductive pathways between the electrodes and the waveform generator,
locating the electrodes such that the biological cells are situated therebetween, and
providing pulse waveforms from the waveform generator to the electrodes, such that the molecules on the electrodes are driven off of the electrodes and delivered into the biological cells,
wherein coating of the electrodes in the electrode assembly with the molecules to be delivered to the biological cells is carried out by the following steps:
preparing a liquid medium in which a quantity of the molecules are carried,
contacting the electrodes with the prepared medium, and
removing the electrodes from the medium and drying off the medium, such that a coating of the molecules remains on the electrodes.

30. A method for delivery of molecules into biological cells, comprising the steps of:
coating electrodes in an electrode assembly with the molecules to be delivered,
attaching the electrode assembly having coated electrodes to an electrode assembly holder,
providing a waveform generator,
establishing electrically conductive pathways between the electrodes and the waveform generator,
locating the electrodes such that the biological cells are situated therebetween, and
providing pulse waveforms from the waveform generator to the electrodes, such that the molecules on the electrodes are driven off of the electrodes and delivered into the biological cells,
wherein coating of the electrodes in the electrode assembly with the molecules to be delivered to the biological cells is carried out by the following steps:
preparing a liquid medium in which a quantity of the molecules are carried,
contacting the electrodes with the prepared medium,
applying pulse waveforms to the electrodes, such that a portion of the molecules are bound to the electrodes, and
removing the electrodes from the medium and drying off the medium, such that a coating of the molecules remains on the electrodes.

31. A method for delivery of polynucleotide vaccine into Langerhans cells in the epidermis of a patient, comprising the steps of:
coating electrodes in an electrode assembly with polynucleotide vaccine, prior to locating the electrodes such that the Langerhans cells are situated therebetween,
attaching the electrode assembly having coated electrodes to an electrode assembly holder,
providing a waveform generator,
establishing electrically conductive pathways between the electrodes and the waveform generator,
locating the electrodes such that the Langerhans cells are situated therebetween, and
providing pulse waveforms from the waveform generator to the electrodes, such that polynucleotide vaccine on the electrodes are driven off of the electrodes and delivered into the Langerhans cells.

32. An apparatus for delivery of molecules into biological cells, comprising:
a waveform generator which provides pulse waveforms,
an electrode assembly holder,
an electrode assembly which is mechanically supported by said electrode assembly holder and which is electrically connected to said waveform generator through electrically conductive pathways, wherein said electrode assembly includes electrodes which are coated with the molecules to be delivered into the biological cells, prior to locating the electrodes such that the biological cells are situated therebetween.

33. The apparatus of claim 32 wherein said electrode assembly is removable and replaceable from said electrode assembly holder.

34. The apparatus of claim 32 wherein:
said electrode assembly includes electrode-assembly-conductive strips, and
said electrode assembly holder includes holder conductors which are registrable with said electrode-assembly-conductive strips when said electrode assembly is mechanically connected to said electrode assembly holder, and wherein said electrode assembly holder includes electrically conductive pathways between said holder conductors and said waveform generator.

35. The apparatus of claim 32, further including:
sterile packaging for said electrode assembly which is removed from said electrode assembly after said electrode assembly is mechanically supported by said electrode assembly holder and is electrically connected to said waveform generator.

36. The apparatus of claim 32 wherein said waveform generator provides pulse waveforms which include a sequence of at least three single, operator-controlled, independently programmed, DC electrical pulses, to the biological cells wherein the sequence of at least three DC electrical pulses has one, two, or three of the following characteristics: (a) at least two of the at least three pulses differ from each other in pulse amplitude; (b) at least two of the at least three pulses differ from each other in pulse width; and (c) a first pulse interval for a first set of two of the at least three pulses is different from a second pulse interval for a second set of two of the at least three pulses.

37. The apparatus of claim 32 wherein said electrodes are in a form of needle electrodes.

38. The apparatus of claim 32 wherein said electrodes include electrically insulated outer surface electrode tip portions and electrically insulated outer surface electrode base portions.

39. The apparatus of claim 32 wherein said electrodes are coated with macromolecules.

40. The apparatus of claim 39 wherein said macromolecules include a polynucleotide vaccine.

41. The apparatus of claim 39 wherein said macromolecules include a solid phase polynucleotide vaccine.

42. The apparatus of claim 39 wherein said macromolecules include a DNA vaccine.

43. A The apparatus of claim 39 wherein said macromolecules include a solid phase DNA vaccine.

44. The apparatus of claim 39 wherein said macromolecules include a RNA vaccine.

45. The apparatus of claim 39 wherein said macromolecules include a solid phase RNA vaccine.

46. The apparatus of claim 39 wherein said macromolecules include a protein-based vaccine.

47. The apparatus of claim 39 wherein said macromolecules include a solid phase protein-based vaccine.

48. An apparatus for delivery of molecules into biological cells, comprising:

a waveform generator which provides pulse waveforms, an electrode assembly holder, and an electrode assembly which is mechanically supported by said electrode assembly holder and which is electrically connected to said waveform generator through electrically conductive pathways, wherein said electrode assembly includes electrodes which are coated with the molecules to be delivered into the biological cells, wherein said electrodes are coated with a solid phase DNA vaccine.

49. A packaged sterile electrode assembly which includes:

a sterile electrode assembly which includes electrodes which are coated with the molecules to be delivered into biological cells, wherein said electrode assembly includes electrode-assembly-conductive strips for connection to electrically conductive pathways to said waveform generator, and an internally sterile package which encloses said sterile electrode assembly contained therein.

50. The packaged sterile electrode assembly of claim 49 wherein said electrodes include electrically insulated outer surface electrode tip portions and electrically insulated outer surface electrode base portions.

51. The packaged sterile electrode assembly of claim 49 wherein said electrodes are in a form of needle electrodes.

52. The packaged sterile electrode assembly of claim 49 wherein said electrodes are coated with macromolecules.

53. The packaged sterile electrode assembly of claim 52 wherein said macromolecules include a polynucleotide vaccine.

54. The packaged sterile electrode assembly of claim 52 wherein said macromolecules include a solid phase polynucleotide vaccine.

55. The packaged sterile electrode assembly of claim 52 wherein said macromolecules include a DNA vaccine.

56. The packaged sterile electrode assembly of claim 52 wherein said macromolecules include a solid phase DNA vaccine.

57. The packaged sterile electrode assembly of claim 52 wherein said macromolecules include a RNA vaccine.

58. The packaged sterile electrode assembly of claim 52 wherein said macromolecules include a solid phase based vaccine.

59. The packaged sterile electrode assembly of claim 52 wherein said macromolecules include a protein-based vaccine.

60. The packaged sterile electrode assembly of claim 52 wherein said macromolecules include a solid phase protein based vaccine.

61. A method for delivery of molecules into biological cells, comprising the steps of:

pre-coating electrodes in an electrode assembly with the molecules to be delivered, attaching the electrode assembly having coated electrodes to an electrode assembly holder, providing a waveform generator, establishing electrically conductive pathways between the electrodes and the waveform generator, locating the electrodes such that the biological cells are situated therebetween, and providing pulse waveforms from the waveform generator to the electrodes, such that the molecules on the electrodes are driven off of the electrodes and delivered into the biological cells.

* * * * *